United States Patent
Kapurniotu et al.

(10) Patent No.: US 6,265,534 B1
(45) Date of Patent: Jul. 24, 2001

(54) SUPERPOTENT CALCITONIN ANALOGS HAVING GREATLY INCREASED HYPOCALCEMIC ACTION IN VIVO

(75) Inventors: Afroditi Kapurniotu; Jurgen Bernhagen, both of Tubingen; Herwig Brunner, Stuttgart, all of (DE)

(73) Assignee: Fraunhofer-Gesellschaft zur Forderung der Angewandten Forschung E.V., Munich (DE)

( * ) Notice: Subject to any disclaimer, the term of this patent is extended or adjusted under 35 U.S.C. 154(b) by 0 days.

(21) Appl. No.: 09/137,389

(22) Filed: Aug. 20, 1998

(51) Int. Cl.[7] .................................................. A61K 38/23
(52) U.S. Cl. ........................ 530/307; 530/318; 514/11; 514/808; 930/60; 930/DIG. 670
(58) Field of Search .................... 514/11, 808; 530/318, 530/307; 930/60, DIG. 670

(56) References Cited
FOREIGN PATENT DOCUMENTS 44 31 121 A1     5/1996   (DE) .

OTHER PUBLICATIONS

Kapurniotu A. et al. J. Med. Chem., 38, 836–847, May 1985.*

Stevenson, J. Invest. Cell Pathol., 3, 187–193, Jan. 1980.*

* cited by examiner

*Primary Examiner*—Michael Borin
(74) *Attorney, Agent, or Firm*—Barnes & Thornburg

(57) ABSTRACT

Superpotent calcitonin analogs have greatly increased hypocalcemic action in vivo. These calcitonins and calcitonin derivatives are employed for the therapy of, for example, osteoporosis, Paget's disease or hypercalcemia. The calcitonins and calcitonin derivatives are distinguished by a bridging of the amino acids present in the positions 17 and 21. By means of suitable choice of the amino acids present in these positions an 18-membered or 19-membered ring is produced. This ring leads to an increased conformational stability and to an increased activity of the modified calcitonin. A particularly suitable hCt (human calcitonin analog) is a cyclo$^{17,21}$-[Asp$^{17}$, Orn$^{21}$]-hCt having a 19-membered ring structure between the lactam-bridged Asp$^{17}$ and Orn$^{21}$.

6 Claims, 1 Drawing Sheet

Figure 1:

SEQUENCE LISTING

<160> NUMBER OF SEQ ID NOS: 2

<210> SEQ ID NO 1
<211> LENGTH: 32
<212> TYPE: PRT
<213> ORGANISM: Homo sapiens
<220> FEATURE:
<221> NAME/KEY: DISULFID
<222> LOCATION: (1)..(7)

<400> SEQUENCE: 1

Cys Gly Asn Leu Ser Thr Cys Met Leu Gly Thr Tyr Thr Gln Asp Phe
 1               5                  10                  15

Asn Lys Phe His Thr Phe Pro Gln Thr Ala Ile Gly Val Gly Ala Pro
            20                  25                  30

<210> SEQ ID NO 2
<211> LENGTH: 32
<212> TYPE: PRT
<213> ORGANISM: Homo sapiens
<220> FEATURE:
<221> NAME/KEY: SITE
<222> LOCATION: (21)
<223> OTHER INFORMATION: Xaa = Orn

```
<221> NAME/KEY: DISULFID
<222> LOCATION: (1)..(7)
<221> NAME/KEY: SITE
<222> LOCATION: (17)..(21)
<223> OTHER INFORMATION: Lactam Bridge between Asp 17 and Orn 21:  Asp
      17 - CH2 - CO - NH - (CH2)3 - Orn 21

<400> SEQUENCE: 2

Cys Gly Asn Leu Ser Thr Cys Met Leu Gly Thr Tyr Thr Gln Asp Phe
 1               5                  10                  15

Asp Lys Phe His Xaa Phe Pro Gln Thr Ala Ile Gly Val Gly Ala Pro
                20                  25                  30
```

SUPERPOTENT CALCITONIN ANALOGS HAVING GREATLY INCREASED HYPOCALCEMIC ACTION IN VIVO

FIELD OF THE INVENTION

The present invention relates to calcitonins and calcitonin derivatives having a hypocalcemic effect. Calcitonins and calcitonin derivatives of this type are employed in particular in the field of the pharmaceutical industry and in the field of medicine, for example for the treatment of osteoporosis, of Paget's disease or of hypercalcemia.

BACKGROUND OF THE INVENTION

Calcitonins are peptide hormones which consist of 32 amino acids. On account of their hypocalcemic effect and of the inhibition of bone destruction caused by them, they have great pharmacological importance. They are therapeutically employed for the treatment of osteoporosis, of Paget's disease or to hypercalcemia. Use is made here, in particular, of the calcitonins of man (hCt), of pig (pCt) or of ultimobranchial species, such as the salmon (sCt) or the eel (eCt).

The calcitonins or their derivatives of ultimobranchial species have a 20- to 50-fold higher activity in vivo than human calcitonin. Therefore these calcitonins are preferably employed for therapeutic purposes. The calcitonins of the ultimobranchial species differ considerably, however, in their amino acid sequence from the peptide of human calcitonin. For example, salmon calcitonin differs in 16 of the 32 amino acids from human calcitonin. Nevertheless, it is used to this day, since on account of its considerably higher activity the dosage for therapeutic purposes can be kept lower.

A disadvantage of calcitonins of ultimobranchial species, however, is that they cause an immune reaction in man on account of the amino acid differences. This high antigenicity leads to antibody formation against the particular calcitonin therapeutically employed, often even six months after the start of administration. This high antigenicity subsequently leads to secondary resistance and desensitization to the calcitonin employed. This necessitates, on the other hand, the administration of higher doses, which in turn lead to higher antibody formation and thus secondary resistance, and also to further side effects (contraindications).

Of the known calcitonins, further derivatives which are more active compared with the native form are known. For example, a replacement of three to five amino acid residues on the hydrophobic side of the potential α-helical region (8–22) of hCt by leucines leads to more active calcitonin analogs. The activity of the calcitonin derivatives is in this case attributed to a close relationship between a potential amphiphilic α-helical region between the amino acid residues 8 and 22 and the biological action of the molecule, on the other hand to the conformational flexibility and the spatial interactions of various molecular regions.

Apart from sCt and α-aminosuberic acid-1,7-eCt, these analogs, however, up to now have no further clinical use for the treatment of the above mentioned diseases.

Since as a result of the high proteolytic degradation rate (in-vivo half-life) of the calcitonins therapeutically employed, at present comparatively high amounts have to be administered, this—as described above—in turn leading to rapid antibody formation (secondary resistance) and possible side effects (contraindications), the increase in the bioactivity or proteolysis resistance is ascribed great importance.

Conformationally stabilized analogs of hCt of this type having increased hypocalcemic action are disclosed in DE 44 31 121 A1. In this specification, hCt derivatives are described in which a 20-membered ring structure is produced by the introduction of a covalent lactam bridge between the amino acids in positions 17 and 21, for example by the amino acid in position 17 being aspartic acid and the amino acid in position 21 being lysine. These hCt analogs have an increased conformational stability and an increased hypocalcemic action.

This hypocalcemic action, however, is still not sufficient in order to make possible therapeutic use of these hCt analogs for the treatment of the diseases described above.

It is the object of the present invention to make available calcitonins or calcitonin derivatives which have an increased conformational stability and a high biological activity.

This object is achieved by the calcitonins and calcitonin derivatives as claimed in the precharacterizing clause of claim 1 in combination with its characterizing features.

DETAILED DESCRIPTION OF THE INVENTION

The calcitonins and calcitonin derivatives according to the invention have a bridge between the amino acids in the positions corresponding to the positions 17 and 21 of human calcitonin. In these positions, amino acids of this type are incorporated such that as a result of the bridge a ring is formed which has 18 or 19 members. In contrast to the 20-membered ring structure known from the prior art, the calcitonins according to the invention are more stabilized with respect to their conformation, such that proteolytic degradation is retarded. Furthermore, these calcitonins and calcitonin derivatives according to the invention have a very high activity, as a result of which a low dosage is possible. Because the sequence is very similar to the human molecule, no immune reaction occurs (no secondary resistance). All in all, it was found that the ring contraction in comparison to the prior art leads to a very high activity, such that a 19-membered or 18-membered ring structure is suitable as a lead structure for further potent calcitonin analogs beyond those described in the examples.

Advantageous embodiments of the calcitonins and calcitonin derivatives according to the invention are described in the dependent claims.

The amino acids in the positions 17 and 21 can be bridged by suitable linkers or, with appropriate choice of the amino acid, via a lactam bridge. Calcitonins have particularly advantageous properties in which aspartic acid and omithine are present in the positions mentioned instead of asparagine and threonine in the human calcitonin. This calcitonin is 360-times more active than the original human calcitonin and still three times more active than calcitonin from salmon (sCt) in a mouse in-vivo test.

By means of the introduction of glutamic acid and α,γ-diaminobutyric acid instead of asparagine and threonine in the positions 17 and 21, a 19-membered ring and a highly active analog Is also produced.

A calcitonin derivative according to the invention having an 16-membered ring results by the replacement of the amino acids asparagine and threonine in the positions 17 and 21 by aspartic acid and α,γ-diaminobutyric acid, respectively. This calcitonin derivative is about 30 times more active than the original human calcitonin.

Several other highly active 19- or 18-membered ring containing analogs are also described in the invention including the following amino acid pairs in the positions 17 and 21 of calcitonin:1,3-diaminopropionic acid and 2-aminoadipic acid, or 1,3-diaminopropionic acid and 2-aminoadipic acid, or 1,3-diaminopropionic acid and 5-carboxymethylcystein, or 5-carboxymethylcyst in and 1,3-diaminopropionic acid, or 2-aminoadipic acid and serin, or serin and 2-aminoadipic acid, or glutamic acid and serin oder serin and glutamic acid.

The mentioned increase in the stability and activity due to the introduction of the 18-membered or 19-membered ring system according to the invention does not only result, however, in the case of human calcitonin, but also in the case of calcitonins of the pig or of the ultimobranchial species such as salmon or eel or their analogs known up to now. For example, the activity of a known highly active analog in which the positions 1 and 7 are replaced by an α-aminosuberic acid reside can be further increased by the introduction of an 18-membered or 19-membered ring as described above. Even in the case of already-known analogs, an improvement in the stability and activity thus results due to the introduction of the 18- or 19-membered ring structure according to the Invention.

Figure 2:
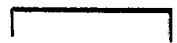
Figure 2:
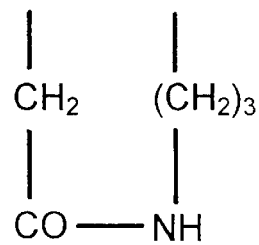

In what follows, some examples of the calcitonins and calcitonin derivatives according to the invention and their preparation are given. The figures show:

FIG. 1 the primary structure of human calcitonin according to the single letter code for amino acids;

FIG. 2 the primary structure of $cyclo^{17,21}$-[$Asp^{17}$,$Orn^{21}$]-hCt according to the single letter code for amino acids.

FIG. 1 shows the primary structure of human calcitonin, Asparagine and threonine are present in the positions 17 and 21, respectively.

FIG. 2 shows a human calcitonin according to the invention in which the amino acids in positions 17 and 21 are replaced by aspartic add and omithine, respectively, and their side chains are connected covalently via a lactam bridge to produce a 19-membered ring. In this case, the amino add sequence is written in the single letter code, but the amino acids 17 and 21 are shown, for better illustration, according to the three letter code and their side chains bonded via a lactam bridge are shown with their structural formulae. Furthermore, the S—S bridge between $Cys^1$ and $Cys^7$ is indicated.

This calcitonin according to the invention has an activity which in the mouse in-vivo test is 363-fold above the activity of the human calcitonin shown in FIG. 1. Advantages of this calcitonin shown In FIG. 2 are consequently Its high activity and Its high conformational stability, which is why a lower dosage is possible for therapeutic purposes, This results in the fact that no secondary resistances are to be expected. Furthermore, this is in this case the first human calcitonin which has a sufficiently high activity for therapeutic use. Since the primary structure besides the replacement of asparagine by aspartic acid only differs slightly from the primary structure of native human calcitonin In a further amino acid (omithine instead of threonine), only very slight to no immune reactions are to be expected, and therefore side effects (such as, for example, secondary resistance) can largely be avoided.

Instead of aspartic acid and omithine in the positions 17 and 21, respectively, a 19-membered ring is also obtained by the use of glutamic acid or α,γ-diaminobutyric acid in these positions, as a result of which a derivative of human calcitonin results which also has a high activity and high stability with, at the same time, an extremely low immune reaction.

As an example of an 18-membered ring, the calcitonin derivative is given here in which the aspartic acid and α,γ-diaminobutyric acid are arranged In the positions 17 and 21, respectively. By this means, a derivative of human calcitonin having an 18-membered ring results, which also has a high activity and high conformational stability, only a slight immune reaction occurring on account of the small differences to the primary sequence of native human calcitonin.

The mentioned improvements in the activity and stability can also be achieved in already-known calcitonins, for example of salmon, eel or pig, or their already-known analogs.

The calcitonins and calcitonin derivatives according to the invention are essentially prepared by peptide synthesis.

In what follows, the synthesis and purification, characterization and testing of the biological activity of $cyclo^{17,21}$-[$Asp^{17}$,$Orn^{21}$]-hCt of FIG. 1 is described.

Synthesis and Purification

For the syntheses of the conformationally stabilized calcitonin analogs described in this invention, the solid-phase method of peptide synthesis is employed in combination with a method for the preparation of cyclic peptides, which are lactam-bridged by mans of the side chains, directly on the polymeric support (resin) according to Felix A. M. et al. (Int. J. Pept. Prot Res. 32 (1988), 441–445). The synthesis of the hCt analog $cyclo^{17,21}$-[$Asp^{17}$,$Orn^{21}$]-hCt is described in detail in what follows:

First, peptide resin (1) (N-Boc-(hCt(22-32))-MBHA) is prepared as follows according to customary methods of solidphase peptide synthesis:

4 g of a p-methylbenzhydrylamine resin, which is present in the form of an HCl salt, with a substitution level of 0.65 mmol/g is first neutralized in a reaction vessel using triethylamine in DMF (dimethylformnamide) and washed with DMF and dichloromethane (DCM). This is followed by the addition of Boc-Pro-OH and DCC in a three-fold excess (7.2 mmol) In dichloromethane (30 ml) and the reaction suspension is shaken for 18 h. The polymer is then washed with DCM, iProOH, DCM and DMF, and the loading of the resin is determined according to the picric acid method (0.62 mmol/g). The remaining free amino groups are acetylated by means of acetic anhydride (26 mmol) and pyridine (26 mmol) In DCM (30 ml) (1 h) and washed as is customary. For the subsequent extension of the peptide chain, the TBTU method (3-fold excess of protected amino acid) in DMF is used. The completeness of the couplings is checked by means of the Kaiser test. For $Ile^{27}$ and $Phe^{22}$, double couplings are carried out The amino acid derivatives are N-Boc-protected, and Thr is employed as Boc-Thr(Bz). For the removal of the Boc group, 50% TFA (trifluoroacetic acid) in DCM is used (30 min). The peptide resin 1 obtained as described above has a substitution of 0.57 mmol/g and is characterized by amino acid analysis and FAB-MS after removal of the peptide from a small part of the peptide resin. One part of the peptide resin obtained as described above (500 mg; 0.17 mmol) is coupled to Boc-Om(Fmoc) (1 mmol) and then acetylated using acetic anhydride (1 mmol) in the presence of pyridine (1 mmol). The "dilute" (substitution level 0.21 mmol/g of resin) peptide resin obtained is then extended up to the amino acid residue $Asp^{17}$ (coupling method as described for 1). In this case, N-Boc-protected amino acid derivatives are used, and $His^{20}$ and $Lys^{18}$ are employed as Boc-Lys(2ClZ) and Boc-His(Bom). The $N^α$-Fmoc group of $Om^{21}$ and the fluorenylmethyl aster (OFm) protection of the β-carboxyl of Asp$^{17}$ are removed by treatment with a 20% strength piperidine solution in DMF (1×1 min: 1×28 min) according to the method of Felix et al. (Felix, A. M. et al., Int J. Pept. Protein Res. 32 (1988) 441–454). The lactam bridging between the side chains of Asp$^{17}$ and Orn$^{21}$ freed of protective groups is then carried out by the addition of BOP (benzotriazol-1-yloxy-tris (dimethylamino)phosphonium hexafluorophosphate) (0.3 mmol) and DIEA (0.34 mmol) in DMF (50 ml) to the peptide resin and subsequent shaking (for 4 h), The cyclization is monitored by the Kaiser test.

After the removal of the coupling reagent, the peptide resin is acetylated as described above. The further extension of the peptide resin thus obtained with N-Boc-protected amino acids is carried out according to the TBTU coupling method. The side chains of the trifunctional amino acids are protected as follows:

Asp(β-OcHz), Cys(S-p-Mb), Glu(γ-OBzl), Thr(Bzl) and Tyr(2BrZ). 100 mg of the NH$_2$-cyclo$^{17,21}$-[Asp$^{17}$,Orn$^{21}$]-hCt-MHBA thus obtained are treated (30 min at −20° C. and 1 h at 0° C.) with a mixture of HF/ansiole/dimethyl sulfilde/p-thiocresol in the ratio 10/1/1/0.2 (v/v/v/w), which also contains cysteine in a final concentration of 0.27 M. The crude product freed of protective groups and removed from the resin is precipitated by addition of ether, washed three times with ether and extracted in 10% acetic acid (4×20 ml) and lyophilized. Air oxidation of this crude product for the closure of the disulfide bridge follows In a 0.1 M NH$_4$HCO$_3$ solution at high dilution (10$^{-4}$ M) in the dark (24 h). The solution is then lyophilized. The crude product thus obtained is purified by preparative reverse-phase HPLC on a C$^{18}$ column. A gradient of 30–70% B is used over 30 min, A consisting of 0.058% TFA in water and B of 0.05% TFA In 90% acetonitrile. The detection of the peptides Is carried out at 220 nm.

The synthesis and purification of the other hCt analogs having a 19- or 18-membered ring structure is carried out analogously.

Characterization

The purity of the cyclo$^{17,21}$-[Asp$^{17}$,Orn$^{21}$]-hCt thus obtained was determined by amino acid analysis. For the demonstration of identity, MALDI-TOF mass spectrometry or electrospray mass spectrometry was additionally employed. The determination of the conformation of the analogs was carried out by circular dichroism spectropolarimetry.

Testing of the biological activity

The biological activity of the analogs was determined by means of a hypocalcemic test in vivo in BALB/c mice.

Table 1 shows the dose-response determination of the hypocalcemic effect of cyclo$^{17,21}$-[Asp$^{17}$,Orn$^{21}$]-hCt in comparison to native human calcitonin (hCt) and calcitonin from salmon (sCt. The biological activity is shown as a percentage [%] activity of the hypocalcemic effect maximally achievable in this test, as is achieved by 2 μg of hCt.

TABLE 1

| Concentration of the peptides (ng/ml) | Cyclo$^{17,21}$-[Asp$^{17}$,Orn$^{21}$]-hCt (%) | hCt (%) | aCt (%) |
|---|---|---|---|
| 10 | 86.8 | 35.2 | — |
| 1 | 76.3 | 15.8 | 63.2 |
| 0.1 | 68.4 | 5.8 | 51.6 |
| 0.01 | 36.8 | — | 21.1 |

What is claimed is:

1. A calcitonin or calcitonin derivative having a bridge between amino acids in positions corresponding to positions 17 and 21 of human calcitonin, wherein the amino acids in positions 17 and 21 are selected from the group consisting of aspartic acid and α,γ-diaminobutyric acid and wherein the amino acids are arranged in these positions so that the ring formed by the bridge has 18 members.

2. The calcitonin or calcitonin derivative as claimed in claim 1, wherein the bridge is a lactam bridge.

3. A calcitonin or calcitonin derivative as claimed in claim 1, wherein the amino acids in the positions 17 and 21 are bridged by suitable linkers.

4. The calcitonin or calcitonin derivative as claimed in claim 1, wherein the amino acid sequence of the calcitonin or calcitonin derivative otherwise corresponds to a sequence of a known calcitonin or a known calcitonin analog wherein the known sequence is from a species selected from the group consisting of human, salmon, eel, and swine.

5. The calcitonin or calcitonin derivative as claimed in claim 2, wherein the amino acid sequence of the calcitonin or calcitonin derivative otherwise corresponds to a sequence of a known calcitonin or a known calcitonin analog wherein the known sequence is from a species selected from the group consisting of human, salmon, eel, and swine.

6. The calcitonin or calcitonin derivative as claimed in claim 3, wherein the amino acid sequence of the calcitonin or calcitonin derivative otherwise corresponds to a sequence of a known calcitonin or a known calcitonin analog wherein the known sequence is from a species selected from the group consisting of human, salmon, eel, and swine.

* * * * *